United States Patent [19]
Johnson et al.

[11] Patent Number: 5,205,822
[45] Date of Patent: Apr. 27, 1993

[54] REPLACEABLE DILATATION CATHETER

[75] Inventors: Kirk L. Johnson, Miami Lakes; Mark N. Inderbitzen, Miramar, both of Fla.

[73] Assignee: Cordis Corporation, Miami Lakes, Fla.

[21] Appl. No.: 713,430

[22] Filed: Jun. 10, 1991

[51] Int. Cl.$^5$ ............................................. A61M 29/00
[52] U.S. Cl. ..................................... 604/96; 606/192; 604/160
[58] Field of Search .................................. 604/95–101, 604/160, 165; 606/191, 192, 194, 195; 128/772

[56] References Cited

U.S. PATENT DOCUMENTS

| | | |
|---|---|---|
| 871,474 | 11/1907 | Buckner . |
| 1,060,665 | 5/1913 | Bell . |
| 2,043,083 | 6/1936 | Wappler . |
| 2,657,691 | 11/1953 | Nordstrom, Jr. . |
| 2,687,131 | 8/1954 | Raiche . |
| 2,883,986 | 4/1959 | DeLuca et al. . |
| 2,936,760 | 5/1960 | Gants . |
| 3,225,762 | 12/1965 | Guttman . |
| 3,435,826 | 4/1969 | Fogarty . |
| 3,467,101 | 9/1969 | Fogarty et al. . |
| 3,731,692 | 5/1973 | Goodyear . |
| 3,757,768 | 9/1973 | Kline . |
| 3,766,924 | 10/1973 | Pidgeon . |
| 3,769,981 | 11/1973 | McWhorter . |
| 3,837,347 | 9/1974 | Tower . |
| 3,882,852 | 5/1975 | Sinnreich . |
| 3,896,815 | 7/1975 | Fettel et al. . |
| 3,978,863 | 9/1976 | Fettel et al. . |
| 4,195,637 | 4/1980 | Gruntzig et al. . |
| 4,198,981 | 4/1980 | Sinnreich . |
| 4,236,521 | 12/1980 | Lauterjung . |
| 4,244,362 | 1/1981 | Anderson . |
| 4,271,839 | 6/1981 | Fogarty et al. . |
| 4,289,128 | 9/1981 | Rusch . |
| 4,290,428 | 9/1981 | Durand et al. . |
| 4,292,974 | 10/1981 | Fogarty et al. . |
| 4,299,226 | 11/1981 | Banka . |

(List continued on next page.)

FOREIGN PATENT DOCUMENTS

| | | |
|---|---|---|
| 867144 | 12/1952 | Fed. Rep. of Germany . |
| 2828447 | 9/1979 | Fed. Rep. of Germany . |
| 2918282 | 11/1980 | Fed. Rep. of Germany . |
| 3028089 | 2/1981 | Fed. Rep. of Germany . |
| 2934628 | 12/1981 | Fed. Rep. of Germany . |
| 3107392A1 | 9/1982 | Fed. Rep. of Germany . |
| 439636 | 6/1912 | France . |
| 591963 | 7/1925 | France . |
| WO86/03129 | 6/1986 | PCT Int'l Appl. . |
| 1251914 | 8/1986 | U.S.S.R. . |
| 1566308 | 4/1980 | United Kingdom . |

OTHER PUBLICATIONS

Ellis, Jr. et al., "Achalasia Of The Esophagus", *Major Problems In Clinical Surgery*, vol. IX, (1969).
Thomson et al., *Diseases Of The Nose And Throat*, 6th Edition, (1955).

(List continued on next page.)

Primary Examiner—C. Fred Rosenbaum
Assistant Examiner—William Lewis
Attorney, Agent, or Firm—Gerstman & Ellis, Ltd.

[57] ABSTRACT

A balloon dilatation catheter comprises a flexible, tubular catheter shaft which carries a dilatation balloon adjacent the distal end. The catheter shaft defines an inflation lumen communicating with the balloon and a guidewire lumen extending at least most of the length of the catheter and extending through the catheter distal end. A longitudinal slit is defined in the catheter shaft between the guidewire lumen and the catheter exterior. This slit longitudinally extends along the majority of the catheter length from a position proximal of the balloon to a position that is at least adjacent the catheter proximal end.

22 Claims, 2 Drawing Sheets

U.S. PATENT DOCUMENTS

| | | |
|---|---|---|
| 4,315,512 | 2/1982 | Fogarty. |
| 4,323,071 | 4/1982 | Simpson et al.. |
| 4,345,491 | 10/1982 | Marbry ............................... 604/160 |
| 4,345,596 | 8/1982 | Young ................................ 604/161 |
| 4,351,341 | 9/1982 | Goldberg et al.. |
| 4,362,150 | 12/1982 | Lombardi, Jr. et al.. |
| 4,367,747 | 1/1983 | Witzel. |
| 4,413,989 | 11/1983 | Schjeldahl et al.. |
| 4,419,095 | 12/1983 | Nebergall et al.. |
| 4,422,447 | 12/1983 | Schiff. |
| 4,439,186 | 3/1984 | Kuhl. |
| 4,444,188 | 4/1984 | Bazell et al.. |
| 4,445,892 | 5/1984 | Hussein et al.. |
| 4,465,072 | 8/1984 | Taheri. |
| 4,467,790 | 8/1984 | Schiff. |
| 4,468,224 | 8/1984 | Enzmann et al.. |
| 4,479,497 | 10/1984 | Fogarty et al.. |
| 4,490,421 | 12/1984 | Levy. |
| 4,526,175 | 7/1985 | Chin et al.. |
| 4,545,390 | 10/1985 | Leary. |
| 4,552,127 | 11/1985 | Schiff. |
| 4,554,929 | 11/1985 | Samson et al.. |
| 4,569,347 | 2/1986 | Frisbie. |
| 4,571,240 | 2/1986 | Samson et al.. |
| 4,573,966 | 3/1986 | Weikl et al.. |
| 4,582,181 | 4/1986 | Samson. |
| 4,585,000 | 4/1986 | Hershenson. |
| 4,597,755 | 7/1986 | Samson et al.. |
| 4,610,662 | 9/1986 | Weikl et al.. |
| 4,616,648 | 10/1986 | Simpson. |
| 4,619,263 | 10/1986 | Frisbie et al.. |
| 4,630,609 | 1/1986 | Chin. |
| 4,637,396 | 12/1986 | Cook. |
| 4,652,258 | 3/1987 | Drach. |
| 4,662,368 | 5/1987 | Hussein et al.. |
| 4,684,363 | 8/1987 | Ari et al.. |
| 4,702,252 | 10/1987 | Brooks et al.. |
| 4,748,982 | 6/1988 | Horzewski et al.. |
| 4,762,129 | 8/1988 | Bonzel. |
| 4,776,846 | 10/1988 | Wells ................................. 604/161 |
| 4,824,435 | 4/1989 | Giesy et al.. |
| 4,827,941 | 5/1989 | Taylor et al.. |
| 4,917,103 | 4/1990 | Gambale et al.. |
| 4,922,923 | 5/1990 | Gambale et al.. |
| 4,988,356 | 1/1991 | Crittenden et al. ................ 606/192 |
| 5,040,548 | 8/1991 | Yock. |

OTHER PUBLICATIONS de Feyter et al., "Short Term Results Of Percutaneous Transluminal Coronary Angioplasty With The Monorail Technique: Experience In The First 1000 Patients", *Am Heart J.*, 63:253–9, (1990).

Bonzel, "A New PTCA System With Improved Steerability, Contrast Medium Application And Exchangeable Intracoronary Catheters" *PTCA Proc. Abstract Course 3*, Center For Cardiology University Hospital, Geneva, Switzerland, (Mar. 1986).

Gruntzig, "PTCA Technique With A Double-Lumen Dilatation Catheter," published in *The Proceedings of the Workshop on Percutaneous Transluminal Coronary Angioplasty*, U.S. Dept. of Health, Education and Welfare, pp. 123–133, (Mar. 1980).

McAuley et al., "Advances in Guidewire Technology," *Am. J. Cardio.*, 53:94C–96C (1984).

21 C.F.R. §870.1–870.1650.

Fogarty Arterial Embolectomy Catheter Instructions, American Edwards Laboratories, pp. 1–4 (Aug. 1984).

Fogarty, Management of Arterial Emboli", Symposium on Peripheral Vascular Surgery, *Surgical Clinics of North America*, vol. 59, No. 4, Aug. 1979.

Fogarty et al., "Adjunctive Intraoperative Arterial Dilation: Simplified Instrumentation Technique," *Arch. Surg.*, vol. 116, pp. 1391–1397 (Nov. 1981).

Fogarty et al., "Combined Thrombectomy and Dilation for the Treatment of Acute Lower Extremity, Arterial Thrombosis," *J. Vasc. Surg.*, vol. 10, No. 5, pp. 530–534 (Nov. 1989).

Fogarty et al., "Intraoperative Coronary Artery Balloon Catheter Dilatation," *Am. Heart J.*, vol. 107, No. 9, pp. 845–851 (Apr. 1984).

Abele, "Balloon Catheters and Transluminal Dilatation: Technical Considerations," *AJR* vol. 135, pp. 135, 901–906 (Nov. 1980).

Waltman et al., "Transluminal Angioplasty: General Rules and Basic Considerations," *Interventional Radiology* pp. 253–272 (1982).

Castaneda-Zunigia, *Transluminal Angioplasty*, pp. 1–26 (1983).

Gruntzig et al., "Current Status of Dilatation Catheters and Guiding Systems," *Am. J. Cardiol.* 53:92C–93C (1984).

Kaltenbach, "The Long Wire Technique—a new technique for steerable balloon catheter dilatation of coronary artery stenosis," *European Heart J.*, vol. 5, pp. 1004–1009 (Dec. 1984).

Kaltenbach, "Neue Technik zur Steuerbaren Ballondilatation von Kranzgefassverengungen", *Zeitschrift fur Kardiologie*, Band 73, Heft 11 at pp. 669–673 (Nov. 1984) (with english translation).

Seldinger, "Catheter Replacement of the Needle in Percutaneous Arteriography," *Acta. Radiologica.*, vol. 39, pp. 368–376 (1952).

Nordenstrom, "Percutaneous Balloon—Occlusion of the Aorta," *Act Radiol.*, vol. 4, pp. 356–374 (1966).

Friedberg, "Dilatation of Esophageal Strictures in Children, Using a Fogarty Balloon Catheter," presented at 33rd Annual Meeting of the Canadian Otholaryngological Society, (Jun. 1979).

Kugimija et al., "The Use of a Fogarty Balloon Catheter for Dilatation of Postoperative Esophageal Stricture," *Kyobe Geka*, vol. 30, No. 5, pp. 419–422. (1970) (with english translation).

Gruntzig, "Transluminal Dilatation of Coronary Stenosis," *Lancet* 1:263 (1978).

Annual Review of Medicine: Selected Topics In Clinical Sciences, Kennedy & Stewart, vol. 35, pp. 514–522 (1984).

Cumberland, D. C., "Percutaneous Transluminal Angioplasty: A Review," *Clinical Radiology*, vol. 34, pp. 25–38 (1983).

Moersch, "Cardiospasm: Its Diagnosis and Treatment," pp. 232–238 (1932).

Kinney et al., "Transluminal Angioplasty: A Mechanical-Pathophysiological Correlation Of Its Physical Mechanisms", *Radiology*, vol. 153, pp. 85–89 (Oct. 1984).

Earlam et al., "Benign Oesophageal Strictures: Historical And Technical Aspects of Dilatation", *The British Journal of Surgery*, vol. 68, No. 12, pp. 829–836 (Dec. 1981).

Portsmann, "Ein Neuer Korsett-Ballonkathetr Zur Transluminalen Rekanelisation Nach Dotter Unter Besonderer Berucksichtigung Von Obliterationen An Den (List continued on next page.)

OTHER PUBLICATIONS

Beckenarterien", *Radiol. Diagn.* (Berl), vol. 14, pp. 239–244 (1973) (with translation).

Fogarty et al., "Peroperative Transluminal Angioplasty", pp. 313–321.

Nordenstrom, "Balloon Catheters for Percutaneous Insertion Into the Vascular System", *Acta Radiology,* vol. 57, pp. 411–416 (Nov. 1962).

Simpson et al., "A New Catheter System For Coronary Angioplasty", *Am. Jour. Cardiology,* vol. 49, pp. 1216–1222 (Apr. 1982).

Dotter, "Transluminal Angioplasty: A Long View", *Radiology,* vol. 135, pp. 561–564 (Jun. 1980).

Zeitler et al., "Results of Percutaneous Transluminal Angioplasty", *Radiology,* vol. 146, pp. 57–60 (Jan. 1983).

Nordenstrom, "New Instruments for Catherization and Angiocardiography," *Radiology,* vol. 85, pp. 256–259 (Jul.–Dec. 1965).

Fogarty et al., "A Method for Extraction of Arterial Emboli and Thrombi", *Surgery, Gynecology & Obstetrics,* pp. 241–243 (Feb. 1963).

Sos et al., "Percutaneous Transluminal Angioplasty," *Seminars in Roentgenology,* vol. XVI, No. 1, (Jan. 1, 1981).

Meier, *Coronary Angioplasty,* pp. 1–34, 44–46, 240, 251–272. (1987).

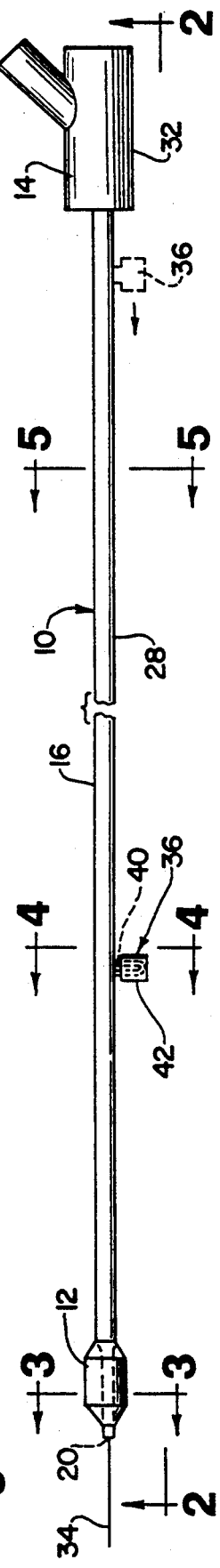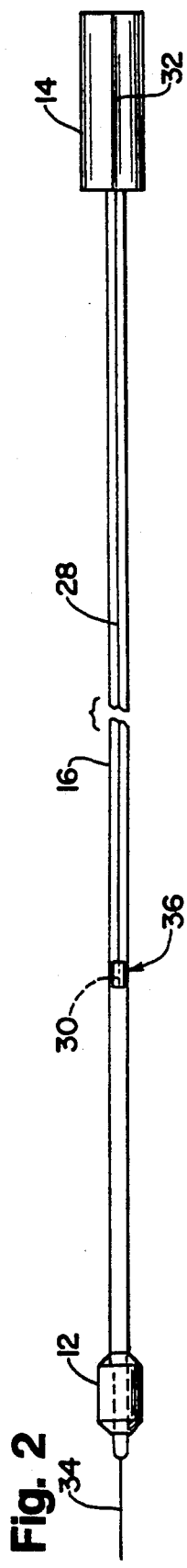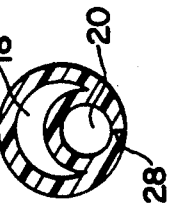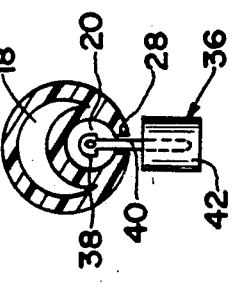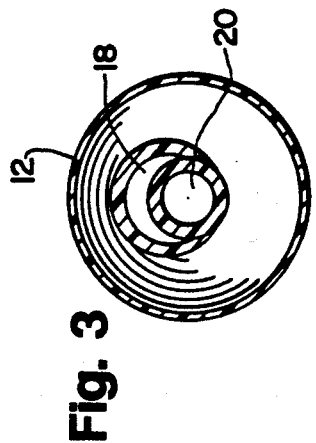

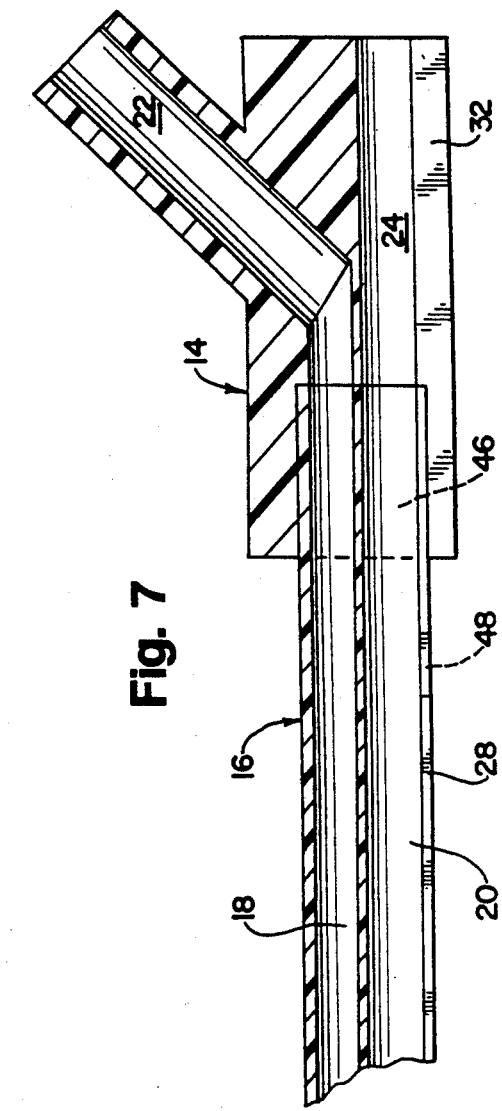
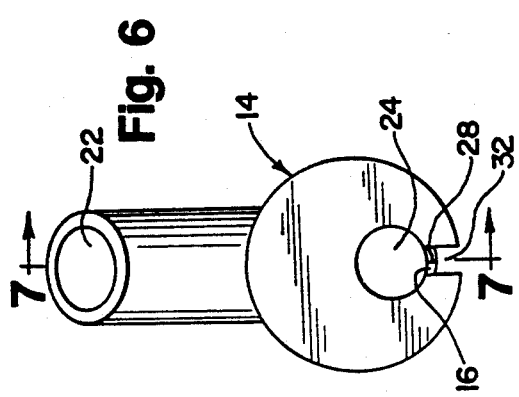
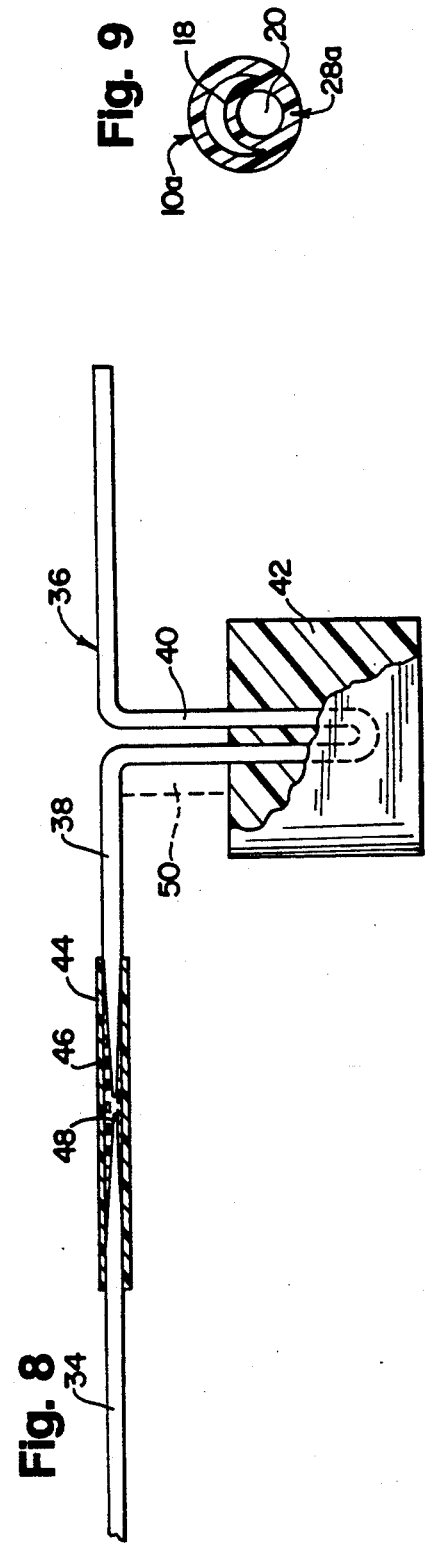

REPLACEABLE DILATATION CATHETER

BACKGROUND OF THE INVENTION

Dilatation catheters are used in particular for dilating arterial lesions or stenoses in the coronary arteries, when such stenoses threaten to seriously obstruct the flow of blood through the artery. Typically, dilatation catheters are emplaced in the coronary artery stenosis by advancing a guidewire which carries a catheter into the coronary artery, and first advancing the guidewire through the constricted aperture at the stenosis. Then, the dilatation catheter, threaded about the guidewire, is advanced therealong until the balloon of the catheter is positioned within the proper area of the coronary artery, after which the balloon is inflated to dilate the artery wall.

In Bonzel U.S. Pat. No. 4,762,129 a dilatation catheter is disclosed in which the guidewire along which the catheter is advanced is retained in a catheter lumen only at an area near the distal end of the catheter, typically being surrounded by the balloon. Along the rest of the catheter length, the guidewire is free and unconnected to the catheter.

An advantage of this is found in the situation when it becomes necessary to remove the catheter without removing the guidewire. With conventional "over the wire" catheters, it is often necessary in this circumstance to install a guidewire extension on the proximal end of the guidewire prior to withdrawing the catheter, so that the guidewire can at all times be gripped and held in stationary position as the catheter is being withdrawn, to avoid the accidental, partial withdrawal of the guidewire along with the catheter. This is of course undesirable since the distal tip of the guidewire may then be pulled out of the constricted stenosis area of the coronary artery, and thus would require repositioning.

While the guidewire extensions described above are in regular clinical use, they are quite inconvenient since they may have to be four feet long or so, extending and coiling all over the operating room in an inconvenient manner.

With the catheter of the Bonzel patent, the use of a catheter extension may be dispensed with, since the guidewire may be gripped by the surgeon at a position which is lateral to the catheter as the catheter is being withdrawn, since the guidewire is not enclosed in a catheter lumen along most of the length of the catheter. Thus, the catheter can be withdrawn while the guidewire is held in its desired position so that it is not accidentally withdrawn along with the catheter.

Horzewski, et al. U.S. Pat. No. 4,748,982 shows another design of dilatation catheter which can be withdrawn from the patient while leaving the guidewire in a desired position within the patient, without the need for a long guidewire extension. Here also, a large portion of the guidewire is positioned laterally of the catheter rather than within a catheter lumen, so that the catheter may be withdrawn while the guidewire is manually gripped and retained in place. Also, the guidewire can pass through a longitudinal slot 36 defined in the catheter of the Horzewski, et al. patent, as described therein.

Both of the catheters disclosed in the patents cited above exhibit significant clinical disadvantages. For example, conventional, over-the-wire dilatation catheters, where the guidewire occupies a catheter lumen throughout most of its length, are better subject to control of the catheter as it is advanced into the arterial system of the patient. Difficulties are encountered in the tracking of catheters which lack a guidewire passing through the great majority of its length. This complicates and renders more difficult the basic advancement technique of such catheters to their desired point of use within the arterial system of the patient. Generally, dilatation catheters having short guidewire-containing lumens relative to their overall length need to carry some other form of stiffener, such as a metal rod or tube, in order to obtain the minimum standards of trackability and pushability. This adds to the complexity and cost of the catheter structure.

Also, in some clinical situations there may be a need to replace the guidewire rather than the catheter after both have been emplaced. This is very difficult to accomplish with the catheters of the two cited patents.

Accordingly, there is a clinical need for a dilatation catheter which exhibits the advantages of the catheters of the cited patents, but which also exhibits the advantages of conventional, over-the-wire catheters, in that they should be easily controllable due to the presence of the guidewire along most or all of the length thereof, with the desired catheter not requiring a stiff, reinforcing rod or tube as part of the catheter itself. Such a catheter needs to have excellent trackability and pushability, while at the same time it can be replaced without the need of a long, cumbersome catheter extension attached to the distal end of the guidewire.

Also, there is a need for a catheter exhibiting all of these advantages, in which, after emplacement of the catheter, the guidewire can be easily replaced rather than the catheter, if that is desired, but the catheter can also be easily replaced when that is desired.

By this invention, a catheter exhibiting the above advantages is provided. The catheter of this invention is very effective both in clinical utility and flexibility, while remaining of low cost and simple construction.

DESCRIPTION OF THE INVENTION

By this invention, a balloon dilatation catheter is provided having proximal and distal ends, with a flexible, tubular catheter shaft which carries a dilatation balloon adjacent the distal end. The catheter shaft defines an inflation lumen which communicates with the balloon, plus a guidewire lumen extending at least substantially the entire length of the catheter and extending through the catheter distal end.

A longitudinal slit is defined in the catheter shaft between the guidewire lumen and the catheter exterior. This slit extends longitudinally along the majority of the catheter length from a position proximal of the balloon to a position that is at least adjacent the catheter proximal end.

Alternatively, the catheter slit may be replaced with an equivalent line of tearing weakness, which may be easily converted into a slit by an object passing therealong, as described in greater detail below.

Preferably, the guidewire lumen is open from the catheter distal end to a position at least adjacent to the proximal end. Typically, the guidewire lumen is open from end to end of the catheter and through the proximal and distal ends. However, if desired, the guidewire lumen may be closed off adjacent the proximal catheter end, and a side aperture may be defined between the guidewire lumen and the catheter exterior adjacent the proximal end. In this circumstance, the slot or line of weakness described above communicates with the side aperture, which aperture serves as an exit port for the guidewire from the guidewire lumen.

Preferably, the catheter of this invention carries a substantially rigid hub at the catheter proximal end. The hub defines a conduit connecting with the guidewire lumen, with the slit of the catheter body described above extending to the hub. A longitudinal slot extends the length of the hub in communication between the hub conduit and the hub exterior. This slot is also aligned with the slit, to permit a sliding member in the slot to slide into the slit, as described below.

Additionally, the hub typically contains a second conduit which communicates with the proximal end of the inflation lumen in the catheter shaft.

Thus, to install the catheter of this invention while holding a guidewire emplaced in the patient in its desired position, one can simply grip the end of the guidewire, typically within the catheter with a tool which fits in the catheter guidewire lumen and carries a transverse handle that can project out of the slit of the catheter, or the line of tearing weakness which has been converted into a slit by the passage of the transverse handle. Thus, the catheter can be installed while gripping the transverse handle, retaining it and the guidewire to which it attaches in a typically stationary position. The guidewire gripping tool with its angled handle is preferably inserted through the proximal end of the catheter, first through the preferred slot of the hub, and then being advanced along the slit into engagement with the guidewire. After such engagement, the catheter can be advanced as desired as the guidewire is firmly retained in its desired position.

To remove the catheter of this invention from implantation about a guidewire within the patient, as one withdraws the catheter, the guidewire can be bent outwardly adjacent its proximal end to penetrate laterally through the slit of the catheter. Thus, the guidewire can be held in stationary position as the catheter is withdrawn.

Alternatively, if the catheter carries a line of tearing weakness rather than an open slit, the above-described guidewire gripping tool may be attached to the proximal end of the guidewire, and the catheter may be withdrawn as the lateral handle of the tool cuts the line of tearing weakness and projects laterally out through the resulting slit thus formed

DESCRIPTION OF THE DRAWINGS

In the drawings, FIG. 1 is an elevational view of the catheter of this invention, showing the gripping tool within the guidewire lumen of the catheter;

FIG. 2 is an elevational view of the catheter of FIG. 1, rotated 90 degrees about its longitudinal axis;

FIG. 3 is a section taken along line 3—3 of FIG. 1;

FIG. 4 is a section taken along line 4—4 of FIG. 1;

FIG. 5 is a section taken along line 5—5 of FIG. 1;

FIG. 6 is an elevational view of the proximal end of the catheter of FIG. I;

FIG. 7 is a fragmentary, sectional view taken along line 7—7 of FIG. 6;

FIG. 8 is an enlarged, elevational view of the guidewire gripping tool with its lateral handle, shown in gripping relation with the proximal end of a guidewire; and FIG. 9 is a cross-section similar to FIG. 5 but showing a modified embodiment of the catheter of FIG. 1, having a line of tearing weakness rather than a slit, which catheter is otherwise identical to that of FIG. 1.

DESCRIPTION OF SPECIFIC EMBODIMENTS

Referring to the drawings, catheter 10 is disclosed, being of a conventional over-the-wire type, but having distinctions from conventional catheters as described herein. Catheter 10 is specifically for angioplasty procedures such as PTCA, carrying an angioplasty balloon 12 adjacent its distal end and a substantially rigid plastic hub 14 at its proximal end.

Flexible, tubular catheter shaft 16 may be made of conventional materials, for example nylon or poly(ethylene terephthalate) having a shore D durometer of about 60–75, specifically about 72. As shown in FIGS. 4 and 5, catheter shaft 10 is made of extruded, double lumen tubing, specifically with an inflation lumen 18 and a guidewire lumen 20, such tubing being manufacturable in accordance with Fontirroche et al. U.S. patent application No. 532,626, filed Jun. 4, 1990 now U.S. Pat. No. 5,063,018. Inflation lumen 18 communicates with the interior of balloon 12, with a portion of catheter shaft 16 being cut away to expose lumen 18 in communication with the tubular balloon 12, which is sealed at both ends to catheter shaft 16, all in a generally conventional manner. Guidewire lumen 20, on the other hand, extends through and is open to the distal end of catheter 10.

As also shown in FIGS. 6 and 7, hub 14 is an integral plastic member that defines a pair of conduits 22, 24. Hub 14 is conventionally sealed to the proximal end of catheter shaft 16, with conduit 22 communicating with inflation lumen 18 and conduit 24 communicating with guidewire lumen 20.

In accordance with this invention, catheter shaft 16 defines a longitudinal slit 28 in its wall, which slit is positioned between guidewire lumen 20 and the catheter exterior as particularly shown in FIG. 5, and which extends along the majority of the catheter length from a position 30 which is proximal of balloon 12 to a position that engages catheter hub 14. As shown in FIG. 5, slit 28 is preferably a normally-closed slit.

Catheter hub 14, being typically made of substantially rigid plastic, defines an open slot 32, slot 32 being aligned with slit 28 to permit a sliding member positioned in slot 32 to slide into slit 28.

Slit 28 typically is spaced a substantial distance from balloon 12 and the distal end of catheter 10. For example, the spacing of distal end 30 of slot. 28 from the catheter distal tip may be at least 27 centimeters in an arterial catheter for angioplasty, which typically may have an overall length on the order of 135 centimeters.

As shown in FIG. 8, a gripping tool 36 may be provided for engaging the proximal end of guidewire 34. The gripping mechanism of gripping tool 36 may be basically similar to the CINCH (T. M.) guidewire extension device, currently on sale by the Cordis Corporation of Miami, Florida. A stiff wire 38 defines a lateral loop or convolution 40 upon which there may be mounted a handle 42 made of plastic or the like, for example by insert molding. The distal end of wire 38 carries a metal sleeve 44, with a coil spring of flat wire 46 being carried therein, and retained by appropriate crimps or dimples in the wall of tube 44. Spring 46 is proportioned so that when the tapered, proximal end 48 of guidewire 34 is inserted into the cylindrical aperture of the coiled spring, the individual coils of spring 46 are stretched outwardly to provide a spring retention thereof. Then, when retention member 36 is pulled rearwardly, the gripping tension of the coil spring 46 against guidewire 34 is increased, rather in the manner of a "Chinese finger trap," so that the end of guidewire 34 is firmly captured and retained therein for a firm connection.

When it is desired to disconnect gripping tool 36 from the guidewire 34, one only has to rotate tool 36 relative to the guidewire 34 in a direction to cause the coils of spring 46 to loosen and open, at which point guidewire 34 is released.

A device incorporating the above principles for the gripping tool 36 is disclosed in U.S. patent application No. 510,523, filed Apr. 18, 1990 and entitled Guidewire Extension System, now U.S. Pat. No. 5,113,872 except that the device illustrated therein does not have a laterally extending wire convolution 40 nor a handle member 42.

The catheter of this invention may be normally used in the conventional manner of a angioplasty catheter, being inserted into the coronary artery of a patient by following a guidewire to direct the catheter balloon 12 to a desired position for inflation of a stenotic portion of an artery. The catheter and guidewire may be advanced together, with the distal tip of the guidewire leading. Alternatively, the surgeon may insert the guidewire into the patient first, positioning its distal end in the stenosis as desired. Then, gripping tool 36 may be inserted into the proximal end of catheter 10, with the side handle 40 thereof projecting first outwardly through slot 32 of hub 14 as tool 36 is advanced, and then advancing into the catheter shaft 16 where handle 40 projects outwardly through slit 28. See FIG. 1.

Then, the proximal end of wire 34 is placed into the distal end of catheter 10, as also shown in FIG. 1. The wire and the catheter are brought together with the catheter advancing along the wire, typically without disturbing the position of the wire in the patient, until the wire 34 connects with tool 36 within the catheter, in the manner of connection illustrated in FIG. 8. Then, by gripping handle 42 of tool 36, one can advance catheter lo along the wire within the patient while holding guidewire 34 in a reliably stationary position. Catheter 10 may thus be advanced until tool 36 exits once again the proximal end of the catheter.

In some circumstances, it turns out that a particular catheter is unsuitable for the clinical situation in hand. In this case, a originally implanted catheter must be withdrawn, but at the same time it is important to cause the guidewire to retain its desired position while the catheter is being withdrawn. In the prior art, to accomplish this it was necessary to attach a lengthy guidewire extension to the proximal end of the guidewire itself, so that a portion of the guidewire extension can be gripped to hold the guidewire in position while the catheter is being withdrawn. Alternatively, when a catheter of the Bonzel '129 or the Horzewski et al. '982 patents is in use a guidewire extension is not needed, but disadvantages of these structures as discussed above are encountered.

The catheter of this invention may be withdrawn from a position of implantation in the patient without using a guidewire extension. Instead, one can grip the proximal end of the guidewire and bend it laterally so that the guidewire protrudes laterally outwardly first through slot 32 of catheter hub 14, and thereafter through slit 28 of catheter body 16. Catheter 10 may be withdrawn from the patient while one holds the laterally projecting portion of the guidewire stationary, while withdrawing the catheter so that the slit 28 thereof slides along the laterally bent portion of the guidewire as the catheter is withdrawn.

Typically, about 50 cm. of the guidewire will project out of the patient with the guidewire properly implanted. Thus, by the time the guidewire reaches the distal end 30 of slit 28, when of proper length the distal end of catheter 10 will have been removed from the patient, so that a portion of projecting guidewire distal to the catheter can be gripped, and the catheter can be taken off the proximal portion of the guidewire that projects out from the patient.

Thus, the catheter of this invention may be withdrawn from its position of implantation in the patient without using a guidewire extension.

Then, another catheter may be inserted on the guidewire in the manner described above.

Contrary to certain prior art, the catheter of this invention can be reliably advanced along a pre-implanted guidewire to a position for example where the balloon 12 occupies a stenosis site in the coronary artery, without changing the guidewire position and without a guidewire extension, while maintaining the important characteristics of good trackability and pushability without the need for added stiffening members carried on the catheter. Catheter 10 may be limp and soft relative to the guidewire, being stiffened and guided by guidewire 34 within lumen 20.

Also, by this invention, the guidewire 34 may be removed from its position while the catheter 10 of this invention is retained in position, by simply holding the catheter in place as the guidewire is pulled out. Thereafter, a fresh guidewire can be installed through catheter 10 to its desired position.

Typically, when a new guidewire is being advanced through catheter 10, it is desirably inserted through conduit 24 of hub 14 by means of a hollow, tubular needle member temporarily placed within conduit 24 to keep the guidewire in a central position as it is advanced.

The catheter of this invention may be modified, if desired, as shown at FIG. 7, by inserting a plug or otherwise closing the proximal end of guidewire lumen 20 as shown in dotted lines at reference numeral 46. Then, an optional side aperture 48 may be provided for the guidewire to be removed. By this means, slot 32 of hub 14 may be eliminated, as well as conduit 24.

Referring to FIG. 9, another modification of the catheter of this invention is shown, apart from which the modified catheter may be identical to the catheter of FIG. 1. In this circumstance, slit 28 of the original catheter is modified to be a line of tearing weakness 28a rather than a slit. Basically, line of tearing weakness 28a is like a slit except for a thin, connecting membrane of material which is relatively easily broken. In this circumstance, it is often desireable for the gripping tool 36 used to carry a cutting blade 50, shown in dotted lines in FIG. 8, to assist in cutting the thin membrane of line of weakness 28a as tool 36 is distally advanced along catheter Thus, by such advancement, line of weakness 28a is turned into a slit similar to slit 28.

An advantage of the structure of FIG. 9 is that the catheter, when originally installed along a guidewire in conventional manner, does not have a slit through which weeping of blood or other fluid may take place. In many clinical angioplasty procedures it is not necessary to replace the catheter, and a catheter similar to FIG. 9 will perform in a manner substantially similar to conventional over-the-wire catheters. However, in the event of the need of catheter replacement, such a catheter may exhibit the advantages of this invention.

When using a catheter of the embodiment of FIG. 9 and such a catheter 10a is in an implanted relation in the patient with guidewire 34, the guidewire typically projects outwardly from the proximal end of hub 14 (FIG. 1), through conduit 24. To remove the catheter from the patient without disturbing guidewire 34, and without using a guidewire extension, one may connect gripping tool 36 to the end of guidewire 34 in the manner shown in FIG. 8. Then, by grasping handle 42 one can hold guidewire 34 with gentle retention as catheter 10 is withdrawn. During the withdrawal process, convoluted wire portion 40 slides first through slot 32 of hub 14, then engaging line of weakness 28a, cutting it with blade 50 and opening it up by the passage of convoluted wire portion 40 as catheter 10 moves rearwardly. This causes tool 36 to move relatively distally of the catheter, although it is the catheter that is moving, i.e., being withdrawn. By this means, guidewire 34 can be retained in its desired position as catheter 10 is withdrawn. When desired, tool 36 may be rotated in the direction to loosen the coils of spring 46, so that the tool 36 and the catheter can be removed from guidewire 34 without disturbing its position.

Then, another catheter 10 or 10a may be applied to guidewire 34 for installation thereof in a manner previously described. The portion of guidewire 34 that projects from the patient is typically much shorter than the length of catheter 10. Thus, gripping tool 36 is inserted into conduit 24 and then into guidewire lumen 20, as before, with the convoluted wire loop 40 passing first through slot 32 and then along slit 28 or line of weakness 28a as tool 36 is advanced. Catheter 10 may be placed onto the proximal end of guidewire 34 and advanced until the proximal end of the guidewire engages tool 36 in the catheter, being positioned at least approximately as shown in FIGS. 1 and 2. When tool 36 is firmly linked With the proximal end of guidewire 34, one can grasp lateral handle 42 to hold guidewire 34 in its desired, implanted position as catheter 10 or 10a is distally advanced along the guidewire. As this happens, tool 36 and guidewire proximal end 48 move relatively proximally of the catheter, first along slit 28 and finally along slot 32 and out of the proximal end of the catheter, as the catheter is implanted into the patient.

The above has been offered for illustrative purposes only, and is not intended to limit the scope of the invention of this application, which is as defined in the claims below.

That which is claimed is:

1. A balloon dilatation catheter having proximal and distal ends, which comprises, a flexible, tubular catheter shaft which carries a dilatation balloon adjacent the distal end, said catheter shaft defining an inflation lumen communicating with said balloon and a guidewire lumen extending at least most of the length of said catheter and extending through the catheter distal end; a longitudinal slit defined in said catheter shaft between the guidewire lumen and the catheter exterior, said slit extending longitudinally along the majority of the catheter length from a position proximal of said balloon to a position that is at least adjacent the catheter proximal end, in which said catheter shaft carries a hub at said proximal end, said hub defining a conduit connecting with said guidewire lumen, said slit of the catheter shaft extending to said hub, and a longitudinal slot extending the length of said hub in communication between said hub conduit and the hub exterior, said slot also being aligned with said slit to permit a sliding member in said slot to slide into said slit.

2. The catheter of claim 1 in which said guidewire lumen is open from said catheter distal end to a position at least adjacent to said proximal end.

3. The catheter of claim 2 in which said guidewire lumen is open from said distal end through said proximal end.

4. The catheter of claim 1 in which said longitudinal slit in the catheter shaft has a distal end that is at least about 27 cm. from the catheter distal end.

5. The catheter of claim 1 in which said guidewire lumen is open from said distal end to a position adjacent said proximal end, and a side aperture defined between said guidewire lumen and the catheter exterior adjacent said proximal end, said slit communicating with said side aperture.

6. A balloon dilatation catheter having proximal and distal ends, which comprises, a flexible, tubular catheter shaft which carries a dilatation balloon adjacent the distal end, said catheter shaft defining an inflation lumen communicating with said balloon, and a guidewire lumen extending the entire length of said catheter and through said proximal and distal ends; a longitudinal slit defined in said catheter shaft between the guidewire lumen and the catheter exterior, said slit longitudinally extending along the majority of the catheter length from a position proximal of said balloon to a position that is at least adjacent the catheter proximal end, said catheter shaft carrying a hub at said proximal end, said hub defining a conduit connecting with said guidewire lumen, said slit of the catheter body extending to said hub, and a longitudinal slot extending the length of said hub and in communication between said hub conduit and the hub exterior, said slot also being aligned with said slit to permit a sliding member in said slot to slide into said slit.

7. The catheter of claim 6 in which said longitudinal slit in the catheter shaft has a distal end that is at least about 27 cm. from the catheter distal end.

8. A balloon dilatation catheter having proximal and distal ends, which comprises, a flexible, tubular catheter shaft which carries a dilatation balloon adjacent the distal end, said catheter shaft defining an inflation lumen communicating with said balloon and a guidewire lumen extending at least most of the length of said catheter, said guidewire lumen extending through the catheter distal end and open from said catheter distal end to a position at least adjacent to said proximal end; a longitudinal slit defined in said catheter shaft between the guidewire lumen and the catheter exterior, said slit extending longitudinally along said catheter from a position proximal of said balloon to a position that is at least adjacent the catheter proximal end, said catheter shaft carrying a substantially rigid hub at said proximal end, said hub defining a conduit connecting with said guidewire lumen, said slit of the catheter shaft extending to said hub, and a longitudinal slot extending the length of said hub and in communication between said hub conduit and the hub exterior, said slot also being aligned with said slit to permit a sliding member in said slot to slide into said slit.

9. The catheter of claim 8 in which said guidewire lumen in open from said distal end through said proximal end.

10. The catheter of claim 9 in which said longitudinal slit in the catheter shaft has a distal end that is at least about 27 cm. from the catheter distal end.

11. A balloon dilatation catheter having proximal and distal ends, which comprises, a flexible, tubular catheter shaft which carries a dilatation balloon adjacent the distal end, said catheter shaft defining an inflation lumen communicating with said balloon and a guidewire lumen extending at least most of the length of said catheter and extending through the catheter distal end; a closed, longitudinal line of tearing weakness defined in said catheter shaft between the guidewire lumen and the catheter exterior, said line of tearing weakness extending longitudinally along the catheter length from a position proximal of said balloon to a position that is at least adjacent the catheter proximal end.

12. The catheter of claim 11 in which said catheter shaft carries a substantially rigid hub at said proximal end, said hub defining a conduit connecting with said guidewire lumen, said longitudinal line of tearing weakness of the catheter body extending to said hub, and a longitudinal slot extending the length of said hub and in communication between said hub conduit and the hub exterior, said slot also being aligned with said line of tearing weakness to permit a sliding member in said slot to engage said line of tearing weakness and to advance along said line of tearing weakness while tearing said line.

13. The catheter of claim 11 in which said guidewire lumen is open from said catheter distal end to a position at least adjacent to said proximal end.

14. The catheter of claim 13 in which said guidewire lumen is open from said distal end through said proximal end.

15. The catheter of claim 13 in which said guidewire lumen defines a side aperture between said guidewire lumen and the catheter exterior, said side aperture being positioned adjacent said proximal end, said line of tearing weakness communicating with said side aperture.

16. A method of emplacing a catheter into a patient where the route of advancement of said catheter into the patient is defined by a pre-installed guidewire having a segment protruding from the patient, said guidewire segment being shorter than the catheter, which method comprises: advancing gripping tool means through the proximal end of a lumen of said catheter while causing a laterally projecting handle of said gripping tool means to engage and project laterally outwardly through a longitudinally extending slit defined in said catheter; relatively advancing the proximal end of said emplaced guidewire through the distal end of said catheter lumen to bring said guidewire proximal end and said gripping tool into engagement, whereby said guidewire proximal end is gripped by the tool; grasping the laterally outwardly projecting handle of said tool while advancing said catheter along said guidewire into the patient toward said implanted catheter site, to prevent advancement of said guidewire, said tool sliding relatively proximally along the slit of said catheter as the catheter is advanced.

17. The method of claim 16 in which said catheter defines a proximal hub defining a conduit communicating with said catheter lumen, and a longitudinal slot extending the length of said hub between the conduit and the exterior, said slot being in communication with said longitudinal slit of the catheter, and including the step of passing the laterally projecting handle through said longitudinal slot prior to engaging said longitudinally extending slit.

18. A method of removing a catheter implanted in a patient with a guidewire occupying a lumen of said catheter at a desired location in the patient, the proximal ends of both said catheter and guidewire projecting outwardly from the patient, which method comprises: gripping a proximal portion of said guidewire; bending said proximal portion of said guidewire in a lateral direction from the axis of said guidewire and catheter while drawing said bent portion of the guidewire outwardly through a longitudinal slit defined in said catheter; and withdrawing said catheter while holding said guidewire adjacent to the projection of said guidewire through said longitudinal slit, to hold said guidewire stationary and to cause said catheter and slit to move proximally relative to said guidewire, whereby said catheter may be removed from the patient while the guidewire remains stationary.

19. The method of claim 18 in which said catheter defines a proximal hub defining a conduit communicating with said catheter lumen, and a longitudinal slot extending the length of said hub between the conduit and the exterior, said slot being in communication with said longitudinal slit of the catheter, and including the step of passing the laterally projecting guidewire portion through said longitudinal slot after engaging said longitudinal slit.

20. The method of claim 19 in which said longitudinal slit of said catheter terminates short of the distal end thereof, a portion of said implanted guidewire extending out of the patient being of greater length than the distance of the distal end of said slit from the distal end of said catheter.

21. The method of withdrawing a catheter from a patient in which the catheter defines a lumen through which a guidewire extends, said guidewire having a segment protruding from the patient, said guidewire segment being shorter than the catheter, which method comprises: advancing gripping tool means through the proximal end of the lumen of said catheter while causing a laterally projecting handle of said gripping tool means to engage and project laterally outwardly through a longitudinally extending slit defined in said catheter; relatively advancing the proximal end of said emplaced guidewire through the distal end of said catheter lumen to bring said guidewire proximal end and said gripping tool into engagement, whereby said guidewire proximal end is gripped by the tool; grasping the laterally outwardly projecting handle of said tool while withdrawing said catheter along said guidewire, to prevent withdrawal of said guidewire along with the catheter, said tool sliding relatively distally along the slit of said catheter as the catheter is withdrawn.

22. The method of claim 21 in which said catheter defines a proximal hub defining a conduit communicating with said catheter lumen, and a longitudinal slot extending the length of said hub between the conduit and the exterior, said slot being in communication with said longitudinal slit of the catheter, and including the step of passing the laterally projecting handle through said longitudinal slot as said handle moves distally along said catheter.

* * * * *